United States Patent
Carter (10) Patent No.: US 12,076,563 B2
(45) Date of Patent: *Sep. 3, 2024

(54) HEARING PROSTHESIS

(71) Applicant: Cochlear Limited, Macquarie University (AU)

(72) Inventor: Paul Michael Carter, Galson (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/076,903

(22) Filed: Dec. 7, 2022

(65) Prior Publication Data

US 2023/0166110 A1 Jun. 1, 2023

Related U.S. Application Data (63) Continuation of application No. 16/646,002, filed as application No. PCT/IB2018/057406 on Sep. 25, 2018, now Pat. No. 11,547,854.

(60) Provisional application No. 62/566,223, filed on Sep. 29, 2017.

(51) Int. Cl.
*A61N 1/36* (2006.01)
*A61N 1/05* (2006.01)
*A61N 1/372* (2006.01)

(52) U.S. Cl.
CPC .......... *A61N 1/361* (2013.01); *A61N 1/0541* (2013.01); *A61N 1/36038* (2017.08); *A61N 1/36053* (2013.01); *A61N 1/36167* (2013.01); *A61N 1/37223* (2013.01)

(58) Field of Classification Search
CPC .. A61N 1/361; A61N 1/36038; A61N 1/0541; A61N 1/36053; A61N 1/36167
See application file for complete search history.

(56) References Cited

U.S. PATENT DOCUMENTS

| | | | |
|---|---|---|---|
| 5,205,285 A * | 4/1993 | Baker, Jr. | A61N 1/36135 607/45 |
| 6,487,453 B1 | 11/2002 | Kuzma et al. | |
| 7,076,308 B1 | 7/2006 | Overstreet et al. | |
| 7,515,966 B1 * | 4/2009 | Litvak | A61N 1/36038 607/57 |
| 8,433,418 B2 * | 4/2013 | DeRidder | A61N 1/361 607/55 |
| 8,666,501 B2 | 3/2014 | Kilgard | |
| 8,885,861 B2 | 11/2014 | Beck | |
| 9,089,692 B2 | 7/2015 | Risi et al. | |
| 9,119,957 B2 * | 9/2015 | Gantz | A61N 1/0541 |
| 9,242,067 B2 | 1/2016 | Shore | |

(Continued)

OTHER PUBLICATIONS

International Search Report and Written Opinion received in related International Application No. PCT/IB2018/057406, dated May 3, 2019 (12 pages).

(Continued)

*Primary Examiner* — Eric D. Bertram
(74) *Attorney, Agent, or Firm* — Edell, Shapiro & Finnan, LLC (57) ABSTRACT

A neural stimulator, suitable for implanting in a recipient, and configured to combine vagal nerve stimulation (VNS) with cochlear stimulation, to result in faster adaptation to new sounds and maps, and alleviation of tinnitus in the recipient.

20 Claims, 5 Drawing Sheets

(56) References Cited

U.S. PATENT DOCUMENTS

| | | | |
|---|---|---|---|
| 9,352,153 B2 | 5/2016 | van Dijk et al. | |
| 9,522,085 B2 | 12/2016 | Kilgard | |
| 9,533,152 B2 | 1/2017 | Kilgard | |
| 10,265,527 B2* | 4/2019 | Lim | A61N 1/36167 |
| 2006/0095088 A1* | 5/2006 | De Ridder | A61N 1/0553 |
| | | | 607/48 |
| 2006/0122675 A1* | 6/2006 | Libbus | A61N 1/0551 |
| | | | 607/116 |
| 2006/0293721 A1 | 12/2006 | Tarver et al. | |
| 2007/0027504 A1* | 2/2007 | Barrett | A61N 2/006 |
| | | | 607/55 |
| 2008/0021517 A1 | 1/2008 | Dietrich | |
| 2008/0234793 A1 | 9/2008 | Gibson | |
| 2009/0005833 A1* | 1/2009 | Cameron | A61N 1/361 |
| | | | 607/45 |
| 2009/0306744 A1 | 12/2009 | Parker et al. | |
| 2010/0191311 A1* | 7/2010 | Scheiner | A61B 5/4047 |
| | | | 607/66 |
| 2011/0077712 A1* | 3/2011 | Killian | A61B 5/12 |
| | | | 607/57 |
| 2012/0277835 A1* | 11/2012 | Della Santina | A61N 1/3605 |
| | | | 607/137 |
| 2013/0072996 A1* | 3/2013 | Kilgard | A61N 1/36171 |
| | | | 607/3 |
| 2013/0226297 A1* | 8/2013 | Mishra | A61N 1/36038 |
| | | | 623/10 |
| 2013/0282070 A1* | 10/2013 | Cowan | A61N 1/36071 |
| | | | 607/45 |
| 2014/0142669 A1* | 5/2014 | Cook | A61N 1/36146 |
| | | | 607/116 |
| 2015/0039057 A1* | 2/2015 | Della Santina | A61N 1/36103 |
| | | | 607/116 |
| 2015/0126802 A1* | 5/2015 | Lim | A61N 1/36082 |
| | | | 607/45 |
| 2015/0360030 A1* | 12/2015 | Cartledge | A61N 1/3603 |
| | | | 607/136 |
| 2016/0279417 A1 | 9/2016 | Kilgard | |
| 2017/0224980 A1* | 8/2017 | Grasso | A61N 1/36036 |
| 2018/0140838 A1 | 5/2018 | Smith | |
| 2018/0339148 A1* | 11/2018 | Kong | A61N 1/37 |

OTHER PUBLICATIONS

Engineer et al., "Reversing Pathological Neural Activity Using Targeted Plasticity," Nature 470(7332) 101-104, Feb. 3, 2011 (15 pages).

"Trigeminal Nerve Stimulation: an overview;" http://www.neurosigma.com/tns/; accessed Mar. 17, 2017 (4 pages).

Extended European Search Report in counterpart European Application No. EP18863119.6, mailed May 18, 2021, 8 pages.

* cited by examiner

HEARING PROSTHESIS

The present application is a continuation application of U.S. patent application Ser. No. 16/646,002, filed Mar. 20, 2020, now U.S. Pat. No. 11,547,854, which is a National Stage application of International Patent Application No. PCT/IB2018/057406, filed Sep. 25, 2018, which claims priority to U.S. Provisional Application No. 62/566,223, filed Sep. 29, 2017.

TECHNICAL FIELD

The technology described herein generally relates to active implantable medical devices, and specifically hearing prostheses.

BACKGROUND

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (such as electrical, optical, and others). Cochlear implants are often proposed when the sensorineural hearing loss is due to the absence or destruction of the cochlea hair cells, which transduce acoustic signals into nerve impulses.

A major task faced by a new cochlear implant recipient is to learn how to interpret the unfamiliar sounds being presented after initial switch-on of the device. This task has been likened to learning a new language.

Attempts to assist habilitation or rehabilitation of new cochlear implant recipients have included expensive and time consuming consultations with audiologists and other clinicians.

Many recipients of cochlear implants for treatment of hearing loss also suffer from tinnitus. Tinnitus is a form of hearing impairment that afflicts millions of people, but its origins are poorly understood and it has proved to be difficult to treat. Symptomatically, a tinnitus sufferer endures the permanent presence of a continuous sound in one or both ears. The sound can be as varied as a constant-pitch buzzing, a whistle, so called "white noise", or a roar. Attempts to treat the condition are hampered by the fact that its origins are poorly understood. Today there is no actual cure, and most approaches are based on a form of "sound masking". At best, to date, the only relief that it has been possible to bring to tinnitus sufferers is to provide a distraction from the noise, rather than a diminution of it.

Most tinnitus suppression devices are, in effect, learning devices: they attempt to train the sufferer to concentrate, consciously at first, and later subconsciously, on frequencies away from the tinnitus frequency.

These recipients could reduce the severity of the impact of tinnitus if they could learn how to concentrate on frequencies away from the tinnitus frequency. A recipient may face similar challenges after an existing implant is adjusted or modified to take account of updated sound processing technology, or as part of the process of optimizing the recipient's overall experience. However, today, there are only a small number of adjustments that can be made to the implant itself. This is despite recent improvements in sound processing strategies and the development of advanced techniques for programming the devices.

Thus, a cochlear implant recipient faces the reality that they will undergo surgery to receive a device which will undoubtedly correct for their hearing loss in a measurable way but may still provide little or no relief from other symptoms such as tinnitus, and may also require considerable effort on the part of the recipient to achieve further gains.

It is desired to at least ameliorate the drawbacks of prior arrangements.

The discussion of the background herein is included to explain the context of the technology. This is not to be taken as an admission that any of the material referred to was published, known, or was part of the common general knowledge as at the priority date of any of the claims found appended hereto.

Throughout the description and claims of the application the word "comprise" and variations thereof, such as "comprising" and "comprises", is not intended to exclude other additives, components, integers or steps.

SUMMARY

The instant disclosure comprises a cochlear implant having an implanted electrode positioned to stimulate the vagal nerve in order to suppress tinnitus (where present) or to improve the learning tasks associated with fitting a cochlear implant such as changing to a new map. The device can also be used to relieve depression or provide any of the other benefits possible with VNS in conjunction with addressing the recipient's hearing loss.

A stimulating electrode, connected via a flying lead, is added to a cochlear implant, and is therefore present in addition to the lead or leads that is/are used to stimulate the cochlea or other auditory nerve cells of the inner ear. The added stimulating electrode may be placed in contact with, such as on, around, or near a branch of the vagus nerve at a convenient site at the time of cochlear implant surgery. In a preferred embodiment, the branch of the vagus nerve that the added electrode contacts will be a cranial branch. Following switch-on of the device, vagal nerve stimulation can be applied under the control of the device while it is used to provide stimulation of the cochlea. If desired, VNS can be coordinated with stimulation of the cochlea so that VNS can be delivered at the best time and frequency to reduce tinnitus and/or improve the recipient's adaptation to a new implant.

An implanted medical device can comprise separate units for cochlear implant and for VNS, and these units can be in communication using one of the known ways of communicating between devices (e.g., wirelessly, or via a direct electrical connection). A single stimulator/receiver may be used to control stimulation of both auditory nerve cells and one or more afferent branches of the vagus nerve. In some embodiments, the stimulation of the vagus nerve branch or branches may be transcutaneous.

The disclosure further comprises a method of suppressing tinnitus in a person suffering from tinnitus, by simultaneously applying a first electrical stimulus to the person's cochlea and a second electrical stimulus to the person's vagus nerve, wherein the first and second stimulus can be continuous or intermittent.

The disclosure still further comprises a method of enhancing a person's learning process after switch-on of a hearing prosthesis, comprising simultaneously applying a first electrical stimulus to the person's cochlea, and applying a second electrical stimulus to the person's vagus nerve.

The disclosure yet further includes a medical device, supplied by itself or within a kit having instructions for use by a surgeon. The medical device includes an implantable neural stimulator, and a physically separate electrode that can be electrically connected to the neural stimulator during surgical implantation.

BRIEF DESCRIPTION OF THE DRAWINGS

Like reference symbols in the various drawings indicate like elements.

DETAILED DESCRIPTION

The disclosure involves using vagal nerve stimulation to enhance the neuroplasticity processes that occur when a recipient receives a cochlear implant. Such processes underlie the recipient's development of ability to learn to listen and understand speech. Stimulation of the vagus nerve can also be used as a means to suppress tinnitus in a recipient of a cochlear implant. The methods herein differ from existing tinnitus suppression methods, which rely on acoustic stimulation in conjunction with VNS.

Figure 1A:
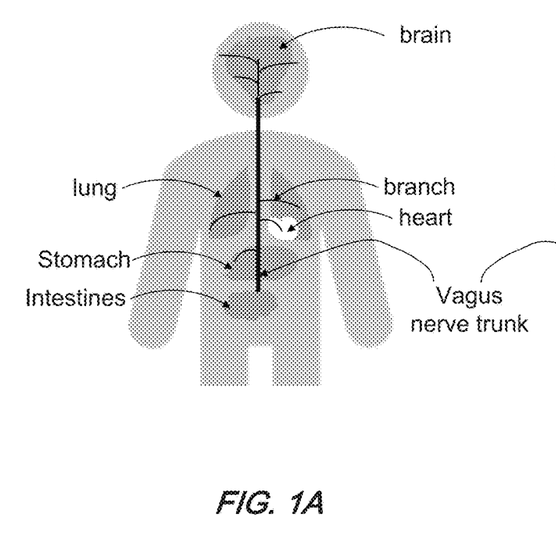
FIGS. 1A and 1B show schematic diagrams of the vagus nerve.

The vagus nerve terminates in the central part of the brain and, via extensive bifurcation, innervates some 30 organs, which include almost all of the internal organs of the body, including the heart, lungs, stomach, spleen, and upper and lower intestines. FIG. 1A shows a schematic of the vagus nerve. It is the primary nerve responsible for the operation of the parasympathetic nervous system—the so-called "rest and digest" system—which works to regulate mood, sleep, digestion and immune response, among other things. For example, after eating a large meal, the vagus nerve is believed to control a person's mood, and possibly also their ability to learn. Eighty percent of the nerve fibers of the vagus nerve are afferent (sensory). In the head and neck region, the vagus nerve innervates the pharynx and larynx as well as the conchae (outer ears).

Figure 1B:
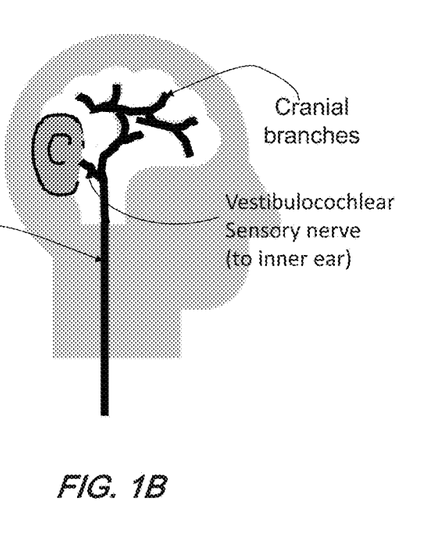

FIG. 1B is a schematic of the upper portion of the vagus nerve, showing a number of cranial branches in a person's brain, including the vestibulocochlear sensory nerve, a branch of the vagus nerve that extends to the ear. There are twelve pairs of cranial nerves, all of which connect the brain to some other part the body. The vagus nerve is different from the other cranial nerves in that it innervates a large number of organs, whereas most of the cranial nerves (e.g., optic nerve, olfactory nerve) primarily connect one organ to the brain. For this reason, the role of the vagus nerve in improved learning and mood is probably unique.

Stimulators used in treatments of nervous system disorders may be chemical, for example the drug Ritalin™, or may be electrical, as provided by devices that deliver controlled amounts of electrical charge to a particular nerve or nerves.

Because of the large number of organs innervated by the vagus nerve and its role in mood and well-being, vagal nerve stimulation (VNS) has been studied as a treatment for a wide range of diseases and conditions including depression, tinnitus, autism, heart failure, various addictions, auto-immune disorders, drug resistant seizures, and chronic inflammatory conditions such as arthritis.

It is possible to stimulate the vagus nerve indirectly, principally via transcutaneous routes, or more effectively via direct electrical stimulation by an implant.

The social isolation associated with hearing loss is known to increase levels of depression, and consequently cochlear implant recipients are more likely than the general population to suffer from depression, due to their general levels of hearing impairment. VNS can therefore also be useful for preventing or alleviating symptoms of depression in cochlear implant recipients.

The disclosure includes a cochlear implant fitted with an additional electrode that can be configured to stimulate a portion of the recipient's vagus nerve, in addition to the stimulation of the person's auditory nerve cells that is achieved by the electrode that is positioned in the recipient's cochlea.

One branch of the vagus nerve, the auricular branch (sometimes termed the Alderman's or Arnold's nerve), runs through the middle ear. The implantation of many cochlear implants comprises drilling a hole through the recipient's mastoid into the middle ear. The vagus nerve is therefore situated a very short distance—often about 1 cm—from where a cochlear implant is positioned.

Furthermore, the auricular branch of the vagus nerve is small and therefore requires less charge to stimulate it than does the main trunk of the nerve.

Figure 2:
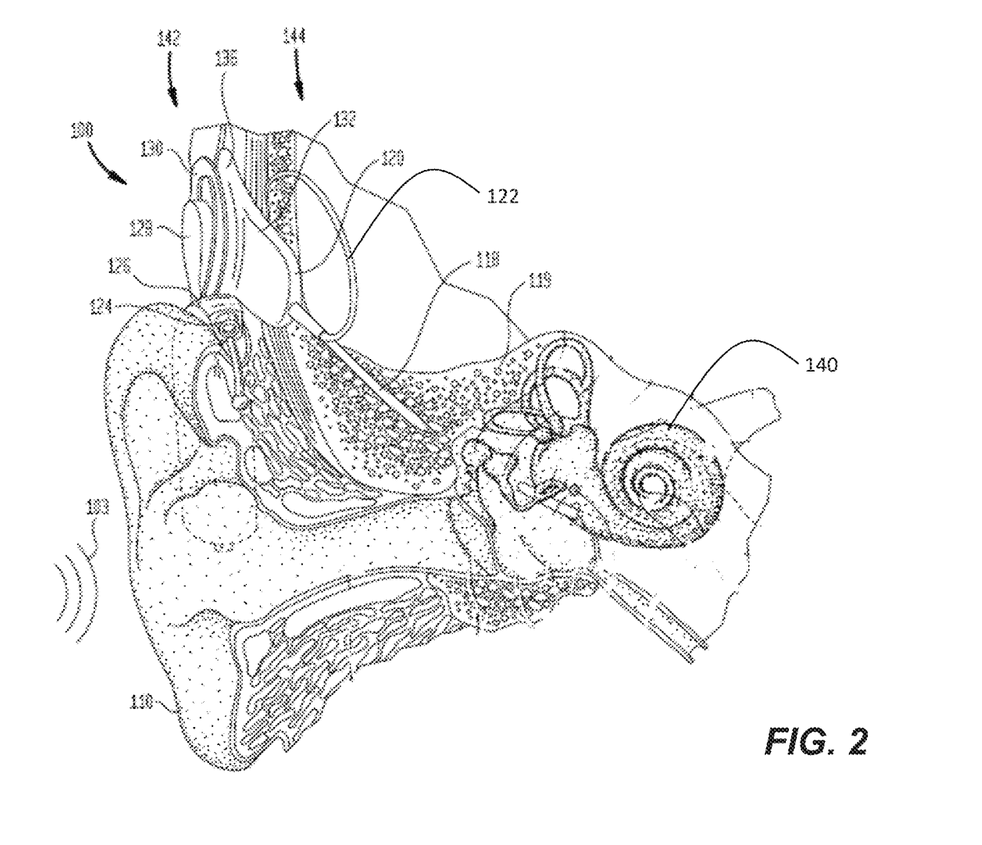
FIG. 2 shows a schematic of a cochlear implant having an electrode configured to stimulate the vagus nerve.

FIG. 2 depicts an exemplary cochlear implant system 100 for use as described herein. System 100 comprises an internal component 144 and an external component 142 having a behind-the-ear (BTE) sound processor 124 that can detect sounds 103, and a separate coil 128/130 that is connected to the BTE processor by a cable (not shown in the drawing).

Internal component 144 has an internal (implanted) receiver/transceiver unit 132, a stimulator unit 120, and an elongate stimulating assembly 118 connected to stimulator unit 120. An additional lead 122, sometimes referred to as a "flying lead" because its flexibility permits it to be placed in a number of positions at the surgeon's discretion, is also connected to stimulator unit 132.

The internal receiver/transceiver unit 132 permits the cochlear implant system 100 to receive and/or transmit signals to a portion 126 of the external component and includes an internal coil 136, and preferably, a magnet (not shown) fixed relative to the internal coil 136. Internal coil 136 can be a wire antenna coil. Internal receiver unit 132 and stimulator unit 120 are hermetically sealed within a biocompatible housing (not shown), and are sometimes collectively referred to as a stimulator/receiver unit. In use, implantable receiver unit 132 may be positioned in a recess of the temporal bone adjacent auricle 110 of the recipient.

Elongate stimulating assembly 118 has a proximal end connected to stimulator unit 120, and a distal end having an intra-cochlea electrode array implanted in cochlea 140. Stimulating assembly 118 extends from stimulator unit 120 to cochlea 140 through mastoid bone 119.

The lead 122 exits the receiver/stimulator at the same location as the stimulating assembly 118. Lead 122 has an electrode disposed at its distal end (not shown in FIG. 2), which in the embodiment shown is embedded in the recipient's muscle tissue adjacent the coil 136. This lead can be positioned so that the distal electrode is in contact with the recipient's vagus nerve.

Various types of energy transfer, such as infrared (IR), electromagnetic, capacitive and inductive transfer, may be used to transfer the power and/or data from external component 142 to the implanted portion of the device. In certain instances of system 100, external coil 130 transmits electrical signals (e.g., power and stimulation data) to internal coil 136 via a radio frequency (RF) link.

In FIG. 2, the sound processor is shown mounted close to the recipient's ear but the technology is not limited to such positioning, and in other embodiments, an off-the-ear (or "button") sound processor can be used. In systems that use a "button" processor, the radiofrequency coil and the external magnet are integrated into a single package. In such embodiments lead 122 is provided with a length sufficient to offer flexibility of positioning, due to the significant variation in position of the processor.

The electrode at the distal end of flying lead 122 can be positioned to stimulate a portion of the vagus nerve located in any of many different parts of a recipient's anatomy. Stimulation can include providing stimulation pulses.

It can be advantageous to change the physical form of the electrode at the distal end of lead 122 to suit its intended purpose and placement, for example, depending on whether it surrounds a section of the vagus nerve (e.g., is a "cuff" electrode), or whether it is embedded in the vagus nerve.

Figure 3:
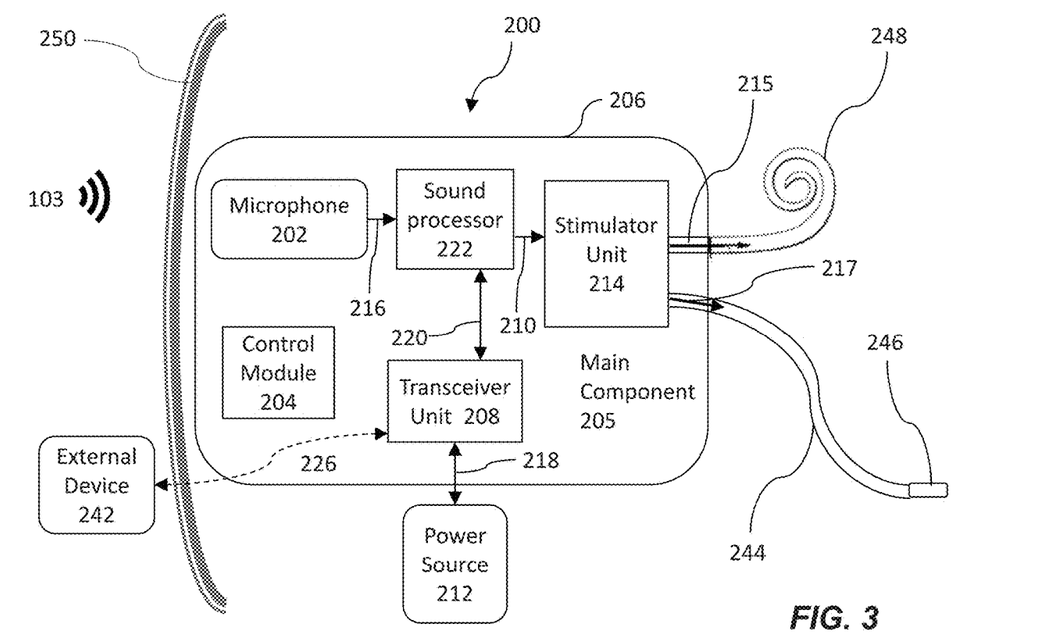
FIG. 3 shows a schematic diagram of a totally implantable cochlear implant having an electrode configured to stimulate the vagus nerve.

FIG. 3 shows schematically a block diagram of a totally implantable cochlear implant system 200 that is configured to simultaneously provide stimulus to a recipient's cochlear as well as their vagus nerve. It is to be understood that, by "at the same time" can include simultaneously such as delivering the two stimuli concurrently, but it also contemplates an interleaved stimulation whereby VNS is delivered alternately with stimulation to the cochlea, the alternations occurring at a frequency that is not easily detectable by the recipient. Totally implanted devices can have a coil/magnet configuration to facilitate coupling with an external component or device 242 such as a charger, or an external sound processor for use in difficult hearing environments.

In system 200, all components are configured to be implanted under one or more layers of skin tissue 250 of a recipient. Therefore, system 200 operates, for at least some of the time, without the need of an external device. An external device 242 can be used to charge an internal battery 212, to supplement the performance of the implanted microphone 202, or when the internal battery no longer functions. External device 242 can be secured in place via a magnetic coupling with a magnet in the implanted portion (not shown in FIG. 3).

System 200 includes a main implantable component 205 having a hermetically sealed, biocompatible housing 206. Disposed in main implantable component 205 is a microphone 202 configured to sense a sound signal 103. Microphone 202 may include one or more components to pre-process the microphone output.

An electrical signal 216 representing sound signal 103 detected by microphone 202 is provided from the microphone to sound processing unit 222. Sound processing unit 222 implements one or more speech processing and/or coding strategies to convert the pre-processed microphone output into data signals 210 for use by stimulator unit 214. Stimulator unit 214 utilizes data signals 210 to generate electrical stimulation signals 215 for delivery to the recipient's cochlea (not shown). In the device of FIG. 3, a stimulating electrode assembly 248 delivers signal 215 to the apex of the cochlea. Stimulator unit 214 also provides electrical stimulation signals 217 to a second electrode assembly 244, having a flying lead portion and a distal electrode 246. The distal electrode 246 is configured to stimulate a portion of the recipient's vagus nerve, for example the auricular branch of the vagus nerve, given its proximity to the implantation site of the cochlear implant.

Cochlear implant system 200 also includes a power source 212. Power source 212 may comprise, for example, one or more rechargeable batteries. Power can be received from a suitably positioned external device 242 and stored in power source 212. The power may then be distributed 218 to the other components of system 200 as needed for operation. For ease of illustration, main implantable component 205 and power source 212 are shown separate from one another. However, power source 212 can alternatively be integrated into the hermetically sealed housing 206, or can be part of a separate module coupled to component 205.

Main implantable component 205 further comprises a control module 204, which can include various components for controlling the operation of implant 200, or specific components of it. For example, controller 204 may control the delivery of power from power source 212 to other components of cochlear implant system 200.

Cochlear implant system 200 further comprises a receiver or transceiver unit 208 that permits the system to transcutaneously receive and/or transmit signals 226 such as power and/or data to/from an external device 242. For example, signals representative of sound detected by an external microphone (not shown) can be transmitted from external device 242 to receiver or transceiver unit 208, and subsequently conveyed to sound processing unit 222 as demodulated or decoded signal 220.

As used herein, transceiver unit 208 refers to any collection of one or more implanted components which form part of a transcutaneous energy transfer system.
Further, transceiver unit 208 includes any number of component(s) which receive and/or transmit data or power, such as, for example, a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data 226 from external device 242 to implantable component 205. To optimize such transfer, external device 242 is magnetically aligned with implantable component 205.

For ease of illustration, cochlear implant system 200 is shown having a transceiver unit 208 in main implantable component 205. In alternative arrangements (not shown), cochlear implant system 200 includes a receiver or transceiver unit which is implanted elsewhere in the recipient outside of main implantable component 205.

Many neural stimulators are equipped with more than one electrical lead, thereby permitting different electrical functions to be performed at different locations within a recipient's anatomy. Some implantable neural stimulators have electrodes located at the end of flying leads, which generally are leads that have some mechanical flexibility in their manner of connection. For example, the Nucleus CI24M auditory prosthesis and other implants from Cochlear Limited, Sydney, Australia, have a flying lead electrode which is usually placed in the temporalis muscle of the recipient. This electrode is present in addition to an electrode array that is positioned in the recipient's cochlea. There may also be an additional "extra-cochlear" electrode on the receiver/stimulator, which is insulated from the implant's housing and acts as a low impedance return-current path. The flying lead electrode can be used as an extra-cochlear reference electrode and is stimulated in parallel with a plate electrode located on or near the implant's receiver/stimulator case. In other embodiments, the flying lead can be used as an alternative to other extracochlear electrodes that are found on the body of the implant.

Figure 4:
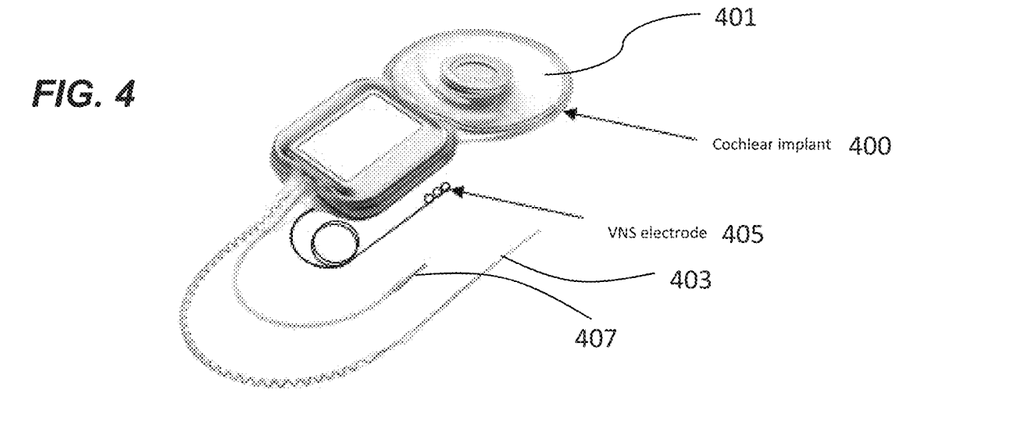
FIG. 4 shows the implantable portion of a hearing prosthesis having a three electrodes.

An exemplary cochlear implant configured to carry out simultaneous vagal nerve stimulation is shown in FIG. 4. Cochlear implant 400 has a transmission coil 401, and three electrodes, and works in conjunction with an external speech processor (not shown). Electrode array 403 is located in the recipient's cochlear. Electrode 405 can be positioned to stimulate a portion of the recipient's vagal nerve. A third electrode 407, optionally present, can be used for a number of different purposes, including as a low-impedance current return path. Other devices may have further optional electrodes, for example as used for functional electrical stimulation.

The various functions of the electrode positioned in the cochlear and the electrode that stimulates the vagus nerve are configurable or programmable within the hardware or firmware of the implant.

In some embodiments, it is more convenient to do a wireless, such as wifi connection rather than run a separate lead to the area where the vagal nerve is to be stimulated. The system is provided as a cochlear implant having a wireless connection to a neck-based vagal nerve stimulator. The cochlear implant combines the two stimulations via a specific timing.

The current levels that can be deployed in the electrode that stimulates the vagus nerve are in the same range as for auditory stimulation (via the electrode positioned in the cochlear). Stimulation of the vagal nerve can require slightly more charge (a few mA) than for cochlear stimulation.

The vagal nerve is most effectively stimulated at a few 10's or 100's of Hz. By contrast, cochlear implants stimulate the nerves of the inner ear at much higher rates (typically 5-10 kHz). Therefore the power required to effect VNS is very small compared to the power consumed by the cochlear implant and there is negligible impact on battery life.

Pulse regimes for stimulation of the vagus nerve vary, depending on the condition. Pulses used are biphasic, current controlled and preferably about 500 □s in duration at about 1 mA current. The auricular branch of the vagus nerve is much smaller than the main trunk of the nerve in the neck, so the charge can be as little as one tenth the value of reported stimulation of the vagus nerve trunk. (For example, 50 □s at 1 mA, or 500 □s at 100 □A). Exemplary ranges include 0.5 seconds of 30 Hz stimulation every 5 minutes for 2.5 hours per day for 20 days. Suitable treatment regimes for depression and epilepsy are 30 seconds every 5 minutes at 30 Hz for several hours per day. A suitable treatment for inflammatory disease is 5 minutes per day at 30 Hz.

A recipient of a cochlear implant today in need of a vagal nerve stimulator would need to have it fitted in a separate surgery, thereby requiring additional time and expense. By contrast, the implant as disclosed herein that is capable of combined VNS and cochlear stimulation has both of the stimulations synchronized, and requires just a single fitting procedure.

Figure 5:
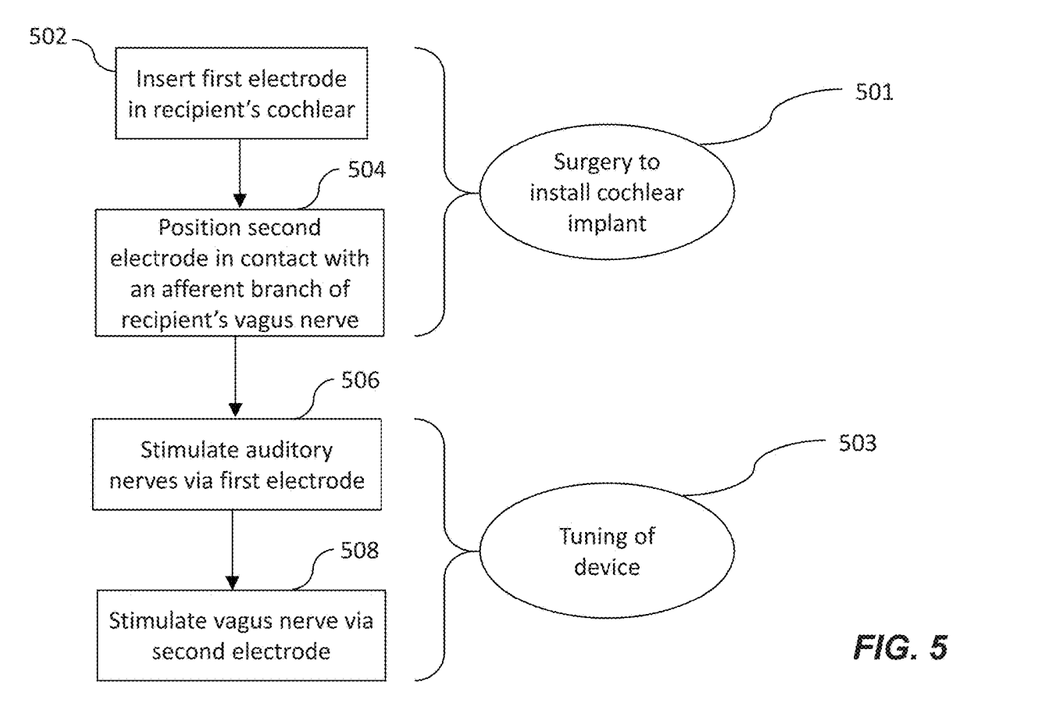
FIG. 5 shows a flow chart of a method herein.

Thus, a method of treating tinnitus in a person suffering from tinnitus, is shown in FIG. 5. The method is divided into two stages: surgery 501 to install the implant, and tuning of the device 503 to deliver the electrical stimulation. Surgically implanting a cochlear implant into an inner ear of the recipient, comprises inserting 502 a first electrode in the person's cochlear, and positioning 504 a second electrode in contact with an afferent branch of the recipient's vagus nerve. Once implanted, the stage of tuning and application to tinnitus treatment includes stimulating 506 auditory nerves by applying an electrical stimulus to the first electrode; and stimulating 508 one or more afferent branches of the vagus nerve by applying an electrical stimulus to the second electrode. The two stimulating operations 506, 508 may be performed concurrently with one another initially, or one can be started and optimized before the other.

Linking the timing of the two stimulations is advantageous in order to target the time for vagal nerve stimulation to be at the most relevant times. In the case of a tinnitus suppression device, VNS is preferably applied at times when the incoming sound is at frequencies far away from the tinnitus frequency, such as different by half an octave (a factor of $\sqrt{2}$ in frequency) or more. It is preferable to base stimulation on sounds separated by at least one octave (factor of two in frequency) from the tinnitus frequency. Sound is logarithmically processed by the cochlea, so octaves are a better indicator than are absolute frequencies. The timing of VNS depends on the frequency spectrum of the incoming sound at any particular point. Application of VNS can also be done in a graduated way, so that VNS was delivered at higher amplitude for frequencies farther from the tinnitus frequency, and at weaker strengths or absent entirely for frequencies close to the tinnitus frequencies. In instances where a recipient experiences tinnitus at more than one frequency, the foregoing considerations apply to each of the relevant tinnitus frequencies.

In another embodiment, a "training mode" can be implemented, wherein incoming sound is deliberately not delivered to the recipient. Instead, particular frequencies separated from the tinnitus frequency are applied to the recipient simultaneously with VNS. In this way, the recipient's auditory cortex undergoes remapping to become less sensitive to frequencies near the tinnitus frequency and more sensitive to frequencies away from the tinnitus frequency. Such an approach is useful where a recipient wishes to practice listening to certain sounds when there aren't necessarily any appropriate sounds in the environment. In this case, special training methods can be provided (a "training mode" for the implant) which deliberately deliver sounds that the user wishes to practice, such as delivered repetitively to reinforce learning. In this case it is usual for the recipient to stop listening to environmental sounds because they may distract from the learning environment. The recipient's sound processor can be switched to control the learning program which will automatically prevent external sounds from reaching the recipient. In some instances, the recipients can receive sound streamed digitally under the control of a mobile device such as a phone or tablet.

In another embodiment, a recipient wishes to enhance their speech or sound recognition performance. There are a range of different aspects of speech and sound which many listeners can find challenging to interpret. Some listeners find particular frequencies challenging to hear, which may arise if they have few remaining ganglion cells at or near the place in the cochlea represented by those frequencies. Other listeners find particular temporal cues difficult to understand. For example, rapidly changing components of speech such as 'plosive' sounds ('t' and 'd' in Ted for example). Other recipients may have trouble differentiating sibilant sounds such as 's' as in 'sat', or 'f' as in fat. Many listeners find distinguishing speech in noise difficult. Others may have trouble hearing certain musical instruments—often those that are spectrally rich such as the pipe organ. In such cases, VNS can be applied when particular sounds known to be challenging for the recipient to recognize are present and are detected by the sound processor. Alternatively, since these sounds relate to particular frequencies, VNS can be applied whenever these frequencies are present in the incoming sound spectrum. Again, this can be done in response to these sounds being heard in the course of the recipient's daily life, or they can be deliberately and repetitively played to the recipient during a 'training mode', at times when the recipient did not wish to listen to incoming sounds. Alternatively, it may be, for example, that rapidly changing temporal cues are difficult for the recipient to distinguish (e.g., 't' as in 'tin' or 'b' as in 'bin'), in which case VNS can be applied whenever these sounds are detected. Again, this can be in response to the sounds being heard during normal listening, or during a training mode.

In a preferred embodiment, the recipient does not have control over switching the stimulation on or off. Instead, the clinician programs the implant and sound processor appropriately during fitting.

In another embodiment, when programming the device to optimize performance in a recipient suffering from tinnitus, sounds are classified into a number of, such as 8, different frequency regions. Each frequency region is associated with one or more electrodes on an electrode array positioned in the recipient's cochlea. The device is enhanced for frequencies away from the recipient's tinnitus frequency (or frequencies).

VNS can be applied, for example, only at times when the cochlear implant is stimulating the recipient's auditory nerve on electrodes that are not associated with the frequencies of the recipient's tinnitus.

The same principle can be applied to delivering VNS at the same time as sound delivered from an existing cochlear implant. In this case the cochlear implant may be paired with a transcutaneous VNS system, which would avoid the patient having to undergo a second surgery to implant a VNS. In general, all four combinations of (non-implantable) hearing aid and cochlear implant with implantable VNS and transcutaneous VNS are possible. The number of surgeries (one or two) depends on how many implantable components are used.

A new cochlear implant recipient faces an immediate challenge: to learn how to interpret new and unfamiliar sounds that are heard after initial switch-on of the device. For many recipients, this challenge can be as complex as learning a new language. VNS is able to increase the rate of language acquisition, and therefore can result in better performance for the recipient in the long term. In this application, VNS can be used primarily after a recipient's device is switched on, but can also be used at later times such as when a recipient is fitted with a new map, or is exposed to a new listening situation such as may occur after a change in job role or a change from a city to a country location, or any change resulting in a substantially new listening environment for the first time. VNS is delivered through an electrode added to the cochlear implant, or it can be delivered through a transcutaneous system which may communicate with the cochlear implant system so that stimulation from both systems can be synchronized by the controller of the cochlear implant. Thus, when programming the device to optimize the learning period for the recipient to appreciate language, the vagus nerve signal is timed appropriately.

Additional Applications of Vagal Nerve Stimulation

Stimulation of other cranial nerves (e.g., the facial nerve) and perhaps nerves of the spinal cord may also be beneficial. Nevertheless, the implant is probably most useful for nerves that are easily accessed from the site of a cochlear implant so that a single receiver/stimulator can be used to drive stimulation of both the auditory nerve and an additional nerve, such as the vagus nerve.

Accordingly, a CI having a lead that can be positioned to stimulate the VN can be used in treatment of conditions other than tinnitus that the recipient may suffer from, due at least in part to the convenience of fitting a combined cochlear implant and VNS in a single surgical procedure. Thus, e.g., depression can be treated in this way. As noted elsewhere herein, cochlear implant recipients are more likely to suffer depression than the general population due to the link between depression, social isolation and hearing loss.

Similarly, cochlear implant recipients can suffer from any of the many diseases for which VNS has been explored as a treatment, and a combined cochlear implant/vagal nerve stimulator can be deployed effectively to treat such conditions.

Exemplary Audioprostheses

The technology described herein can be adapted to work with any type of hearing device that is fitted to a recipient. Such devices include audioprostheses generally, such as acoustic hearing aids and cochlear implants, including totally implantable cochlear implants. The devices include those that function via bone conduction, those that work in the middle ear, and various combinations of such hearing device types. The technology herein is also compatible with other hearing devices that are worn off the ear.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the scope of the appended claims.

What is claimed is:

1. A medical device comprising:
   a stimulation component comprising one or more electrodes configured to be implanted in a recipient adjacent to a vagus nerve of the recipient;
   a microphone configured to receive one or more sounds;
   a sound processing unit configured to convert the one or more sounds received by the microphone of the medical device into one or more data signals; and an implantable stimulator unit configured to use the one or more data signals to generate electrical stimulation signals for delivery to the vagus nerve of the recipient via the one or more electrodes.

2. The medical device of claim 1, wherein the electrical stimulation signals are configured to remediate tinnitus symptoms of the recipient.

3. The medical device of claim 1, wherein the one or more data signals are generated based upon at least one frequency of the one or more sounds received by the microphone of the medical device.

4. The medical device of claim 1, wherein the one or more electrodes comprise a plurality of electrodes.

5. The medical device of claim 1, wherein the medical device comprises:
a second stimulation component configured to be implanted in an ear of the recipient, and
wherein the sound processing unit and the implantable stimulator unit are configured to determine stimulation signals based upon at least one sound of the one or more sounds received by the microphone of the medical device for delivery to the ear of the recipient via the second stimulation component.

6. The medical device of claim 5, wherein the second stimulation component comprises at least one electrode configured to electrically stimulate auditory nerve cells of the recipient, and wherein the sound processing unit and the implantable stimulator unit are configured to determine electrical stimulation of the auditory nerve cells for delivery via the at least one electrode based upon the at least one sound of the one or more sounds received by the microphone of the medical device.

7. The medical device of claim 6, wherein the at least one electrode comprises a plurality of electrodes.

8. The medical device of claim 6, wherein the medical device is configured to independently electrically stimulate the auditory nerve cells and the vagus nerve.

9. The medical device of claim 6, wherein medical device is configured to substantially simultaneously electrically stimulate the auditory nerve cells and the vagus nerve.

10. The medical device of claim 1, wherein the one or more electrodes are configured to electrically stimulate a portion of the vagus nerve in a neck of the recipient.

11. The medical device of claim 1, wherein the one or more electrodes are configured to electrically stimulate an auricular branch of the vagus nerve of the recipient.

12. A method, comprising:
receiving one or more sounds at a medical device, wherein the medical device comprises a microphone configured to receive the one or more sounds and one or more electrodes configured to be implanted proximate to a vagus nerve of a recipient;
generating one or more electrical stimulation signals based on the one or more sounds received by the microphone of the medical device; and
delivering the one or more electrical stimulation signals to the vagus nerve of the recipient via the one or more electrodes.

13. The method of claim 12, wherein generating one or more electrical stimulation signals based on the one or more sounds comprises:
generating the one or more electrical stimulation signals configured to, when delivered to the vagus nerve, remediate tinnitus symptoms of the recipient.

14. The method of claim 12, wherein generating one or more electrical stimulation signals based on the one or more sounds comprises:
generating the one or more electrical stimulation signals based upon at least one frequency of the one or more sounds received by the microphone of the medical device.

15. The method of claim 12, further comprising:
generating one or more second stimulation signals based upon the one or more sounds received by the microphone of the medical device; and
delivering the one or more second stimulation signals to an ear of the recipient.

16. The method of claim 15, wherein the medical device comprises at least one electrode configured to electrically stimulate auditory nerve cells of the recipient, and wherein the method further comprising:
generating one or more second electrical stimulation signals based upon the one or more sounds received by the microphone of the medical device; and
delivering the one or more second electrical stimulation signals to the auditory nerve cells via the at least one electrode.

17. The method of claim 16, further comprising:
independently delivering the one or more electrical stimulation signals to the vagus nerve of the recipient and the one or more second electrical stimulation signals to the auditory nerve cells of the recipient.

18. The method of claim 16, further comprising:
substantially simultaneously delivering the one or more electrical stimulation signals to the vagus nerve of the recipient and the one or more second electrical stimulation signals to the auditory nerve cells of the recipient.

19. The method of claim 12, wherein delivering one or more electrical stimulation signals to the vagus nerve of the recipient comprises:
delivering the one or more electrical stimulation signals to a portion of the vagus nerve in a neck of the recipient.

20. The method of claim 12, wherein delivering one or more electrical stimulation signals to the vagus nerve of the recipient comprises:
delivering the one or more electrical stimulation signals to an auricular branch of the vagus nerve of the recipient.

* * * * *